(12) United States Patent
Haynes et al.

(10) Patent No.: US 6,591,998 B2
(45) Date of Patent: Jul. 15, 2003

(54) LEAKPROOF CONTAINER FOR IMPLANTABLE PROSTHETIC DEVICE

(75) Inventors: Clinton A. Haynes, Mason, OH (US); Reginald D. Fortson, Cincinatti, OH (US); Kenneth D. Waeber, Loveland, OH (US); Douglas L. Marriot, South Lebanon, OH (US); Thomas William Lytle, IV, Round Rock, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 24 days.

(21) Appl. No.: 09/745,684

(22) Filed: Dec. 21, 2000

(65) Prior Publication Data

US 2002/0079286 A1 Jun. 27, 2002

(51) Int. Cl.[7] .............................................. B65D 45/30
(52) U.S. Cl. ........................ 215/276; 220/304; 206/438
(58) Field of Search ................................ 215/273, 274, 215/276, 277, 278, 283, 295, 303, 304, 352; 220/288, 304, 319, 315; 206/438

(56) References Cited

U.S. PATENT DOCUMENTS

| | | | | |
|---|---|---|---|---|
| 3,491,908 A | * | 1/1970 | Beimers | 215/276 |
| 3,838,785 A | * | 10/1974 | Lancesseur | 215/277 |
| 4,034,886 A | * | 7/1977 | Galer | 220/288 |
| 4,093,094 A | * | 6/1978 | Smalley et al. | 215/276 |
| 4,101,031 A | | 7/1978 | Cromie | |
| 4,211,325 A | * | 7/1980 | Wright | 206/438 |
| 4,694,970 A | * | 9/1987 | Hayes | 215/276 |
| 4,801,015 A | | 1/1989 | Lubock et al. | |
| 4,807,770 A | * | 2/1989 | Barriac | 215/276 |
| 5,520,487 A | | 5/1996 | Decker | |
| 5,560,487 A | | 10/1996 | Starr | |
| 5,562,729 A | | 10/1996 | Purdy et al. | |
| 5,720,391 A | | 2/1998 | Dohm et al. | |
| 5,823,342 A | * | 10/1998 | Caudillo et al. | 206/438 |
| 5,824,036 A | | 10/1998 | Lauterjung | |
| RE36,132 E | | 3/1999 | Heacox | |
| 5,875,915 A | * | 3/1999 | Bradshaw et al. | 215/276 |
| 6,102,945 A | | 8/2000 | Campbell | |
| 6,158,604 A | * | 12/2000 | Larguia, Sr. et al. | 215/277 |
| 6,199,696 B1 | * | 3/2001 | Lytle et al. | 206/438 |

FOREIGN PATENT DOCUMENTS

| | | |
|---|---|---|
| DE | 843805 | 7/1952 |
| EP | 0 312 833 | 4/1989 |
| WO | WO 85/01030 | 3/1985 |
| WO | WO 97/48350 | 12/1997 |

* cited by examiner

Primary Examiner—Nathan J. Newhouse
(74) Attorney, Agent, or Firm—Williams, Morgan and Amerson

(57) ABSTRACT

A packaging for an implantable medical device such as a heart valve wherein the implantable medical device is immersed in a liquid medium. The packaging comprises a jar and a lid assembly having a seal and a ridge therebetween, the ridge being adapted to contact the seal. At least one circumferential leg is interposed between the lid assembly and the jar. The leg maintains a predetermined spacing between the lid and the jar and may be loaded in compression. The lid assembly may comprise a lid and an overcap. The overcap may turn independently of the lid and may apply compressive pressure to the lid over the ridge and seal. The lid and overcap may be coupled together by, for example, mating snap hooks. At least one of the lid or overcap may have a plurality of snap hooks. At least one of the plurality of snap hooks may be of different length than other of the snap hooks, whereby an asymmetric force may be applied to the lid when the overcap is loosened from the jar.

33 Claims, 4 Drawing Sheets

LEAKPROOF CONTAINER FOR IMPLANTABLE PROSTHETIC DEVICE

TECHNICAL FIELD

The present invention pertains to packaging for implantable prosthetic devices and in particular to leakproof packaging for prosthetic devices packaged in liquid media.

BACKGROUND ART

Prosthetic heart valves are representative of numerous implantable medical devices that must be stored for long periods of time in a sterile package or in sealed, antibacterial packaging. Often such packages contain a liquid, which may have antibacterial properties to inhibit transmission of disease with the implantable device. To effectively package a heart valve in a liquid storage medium, it is important to have a container that can be manipulated within a sterile environment such as a glove box. The assembled container should provide a seal that will inhibit the loss of the liquid storage medium for a substantial period of time, for example, for as long as five years. Despite the need for a reliable seal, however, it should not be difficult for operating room staff to open the container in the sterile and constrained circumstances of open-heart surgery, where it is anticipated that the present invention will be used.

Today, there are three major types of heart valves: mechanical valves, bioprosthetic or tissue valves, and polymer valves. The term "mechanical valve" as used herein, refers to a heart valve made exclusively of rigid synthetic materials and which comprises essentially no biological components. The term "bioprosthetic valve," on the other hand, refers to a heart valve comprising at least some biological components such as tissue or tissue components (e.g., collagen). The biological components are obtained from a donor animal (typically bovine or porcine), and the valve may comprise either biological materials alone or biological materials with man-made supports or stents. Polymer valves, on the other hand, are heart valves made of at least some elastomeric polymer components, including specifically leaflet occluders made of elastomeric polymers. The present invention is suitable for use in connection with all three major types of heart valves.

Mechanical heart valves are generally characterized by a rigid annular valve body supporting one or more occluders, with a sewing ring or sewing cuff circumscribing the annular valve body. Pyrolytic carbon is a material often used for the valve body or the occluders, although other materials such as metal, polymers or ceramics have also been proposed. The sewing ring is often comprised of silicone rubber with a polymeric fabric cover (e.g., Dacron™ fabric). A metal stiffening ring may be provided between the valve body and the sewing ring and a metal lock wire may be used to secure the stiffening ring and/or sewing ring to the valve body.

A bi-leaflet mechanical valve typically comprises an annular valve body in which two opposed leaflet occluders are pivotally mounted. Monoleaflet mechanical heart valves typically comprise a single leaflet occluder coupled to the annular valve body. Monoleaflet valves typically open by pivoting movement, although some valves open by a combination of pivoting and translational movement. For both bi-leaflet and monoleaflet mechanical valves, the occluders are typically substantially rigid, although some designs incorporate flexible leaflets. In bi-leaflet valves, the leaflets move between a closed position in which the two leaflets are mated to prevent blood flow in the reverse direction, and an open position in which the occluders are pivoted away from each other to permit blood flow in the forward direction. In monoleaflet valves, the leaflet pivots and/or translates from the closed to the open position to allow blood flow. In each case, however, the energy of blood flow causes the occluders to move between their open and closed positions.

Mechanical valves have also been made with flexible leaflets fabricated from man-made materials such as polyurethane, silicone rubber or other biocompatible polymer, for example, a valve described by Purdy, et al., U.S. Pat. No. 5,562,729, incorporated herein by reference. A sewing ring is provided for mounting flexible leaflet mechanical heart valves in a patient's heart.

Bioprosthetic heart valves, in contrast to mechanical valves, comprise an annulus formed by an annular stent to which three flexible leaflets, comprised of a biological material such as bovine or porcine pericardium, are coupled. When blood flows in the forward direction, the energy of the blood flow deflects the leaflets away from the center of the annulus and allows blood to flow in the forward direction. When the pressure across the valve reverses and blood begins to flow in the reverse direction, the three leaflets engage each other in a coaptive region, occluding the valve body annulus and preventing the flow of blood through the valve in the reverse direction. The valve leaflets are made from tissue, such as specially treated porcine or bovine pericardial tissue.

Mechanical heart valves have usually been packaged in containers that support the mechanical valve in such a way as to protect or isolate it from mechanical shocks. Representative packaging patents include Cromie, U.S. Pat. No. 4,101,031; Lubock et al., U.S. Pat. No. 4,801,015; Dohm et al., U.S. Pat. No. 5,720,391; and Caudillo et al., U.S. Pat. No. 5,823,342, all of which are hereby incorporated herein by reference in their entirety. Mechanical valves are typically shipped and stored in a sterilized condition in airtight containers. Because mechanical valves do not comprise biological materials, air is used as the medium in the containers. Inclusion of a liquid storage medium, such as an antibacterial solution, has been deemed unnecessary at best, and possibly damaging to the structural materials during storage, and has been avoided on the basis of added cost as well as the risk of possible harm to the valve. However, Pathak and Chinn have suggested, in a co-pending application filed contemporaneously with the present Application, that liquids may also be advantageously used in mechanical heart valve packaging.

Bioprosthetic valves, on the other hand, are almost always shipped or stored in liquid media because of the need to maintain the biological components of the valve in a hydrated condition. In addition, the medium may have anti-bacterial properties or additives to ensure sterility and protect the biological components from bacterial degradation.

To effectively package a heart valve—whether mechanical or bioprosthetic—in a liquid medium, it is important to have a container that can be manipulated within a sterile environment such as a glove box. The assembled container should provide a seal that will inhibit the loss of the liquid medium for a substantial period of time, for example, for as long as five years. In addition to the need for a reliable seal, however, the container should be easy for operating room staff to open in the sterile and constrained circumstances of open-heart surgery, where it is anticipated that the present invention will be used.

BRIEF SUMMARY OF THE INVENTION

The present invention comprises packaging for an implantable prosthesis such as a heart valve, wherein the prosthesis is immersed in a liquid medium in the container, which may optionally have antibacterial properties. The packaging comprises a jar and a lid assembly having a seal and a ridge therebetween, the ridge being adapted to contact the seal. At least one circumferential leg is interposed between the lid assembly and the jar. The leg maintains a predetermined spacing between the lid and the jar and may be loaded in compression. The lid assembly may comprise a lid and an overcap. The overcap may turn independently of the lid and may apply compressive pressure to the lid over the ridge and seal. The lid and overcap may be coupled together by, for example, mating snap hooks. At least one of the lid or overcap may have a plurality of snap hooks. At least one of the plurality of snap hooks may be of a length different than the other snap hook(s), whereby an asymmetric force may be applied to the lid when the overcap is loosened from the jar.

It is an object of the invention to provide a package for an implantable prosthetic device comprising a jar and lid assembly, the lid assembly having a lid connected to an overcap.

Another object of the invention is to provide a package that is easily assembled in a sterile environment.

Yet another object of the invention is to provide a package that maintains a seal for long periods of time but wherein resistance or friction associated with opening the package is reduced.

A further object of the invention is to provide a package comprising a jar and lid assembly with a seal interposed between the jar and lid assembly.

Another object of the invention is to provide a structure whereby a pre-load between the lid assembly and the jar that is not supported by the seal to maintain loads on the seal within acceptable parameters.

A further feature of the invention is a pre-load structure comprising radially spaced annular legs adjacent an annular seal, the legs contacting an overcap and a jar and adapted to receive a compressive pre-load between the overcap and the jar.

It is also an object of the invention to provide a lid assembly comprising a lid and overcap that are rotatably connected.

Another feature of the invention is a lid and overcap that are connected by mating snap hooks.

Yet another feature of the invention is an arm structure on an overcap for applying compressive force through a lid to a seal.

These and other features and advantages of the invention will be apparent from the following description and accompanying drawings.

DETAILED DESCRIPTION OF THE INVENTION

Figure 1:
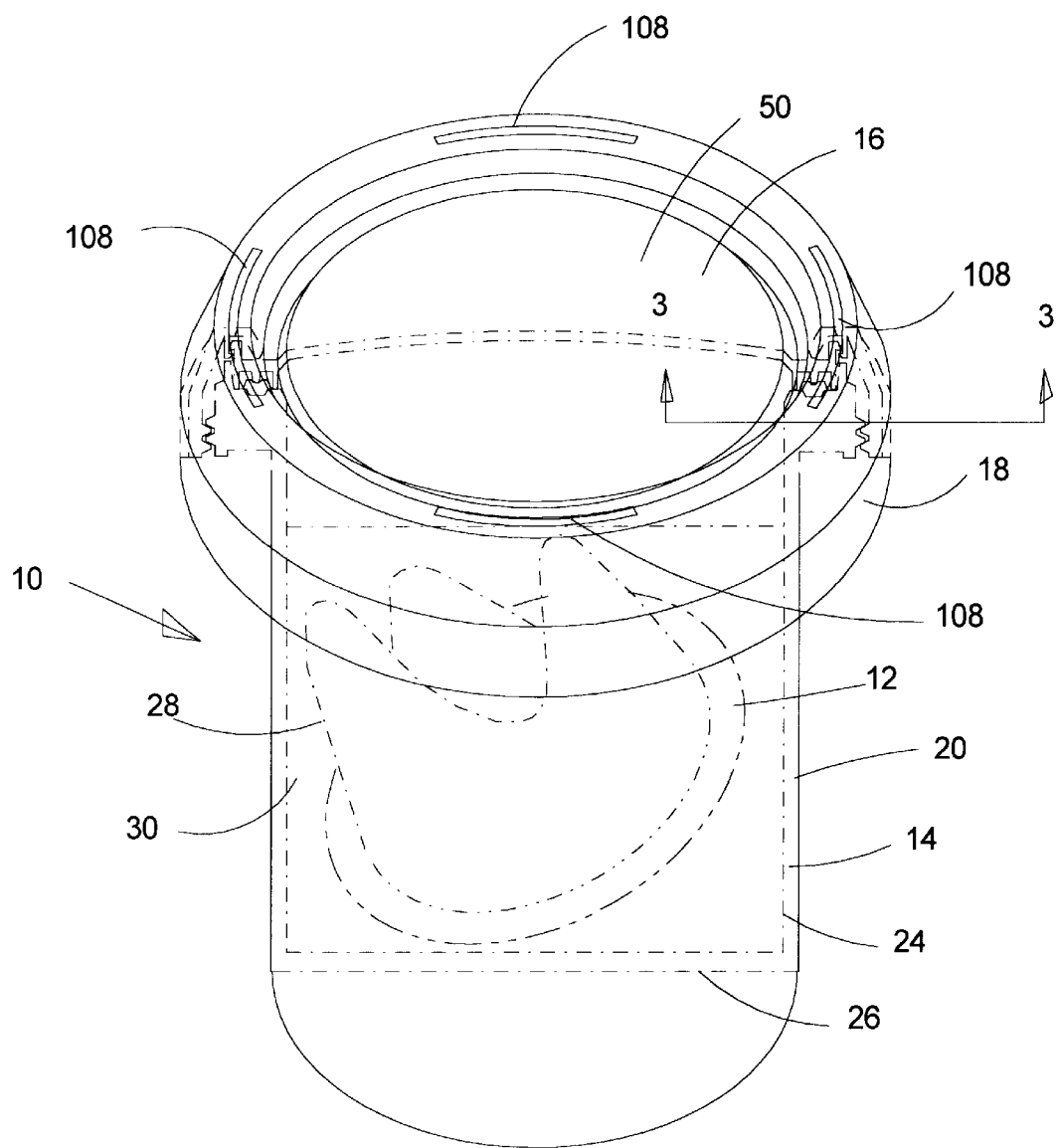
FIG. 1 is an isometric view of a container with a mechanical heart valve in antimicrobial fluid.

FIG. 1 is a perspective view of a package 10 for a prosthetic device such as heart valve 12, shown in phantom lines. Heart valve 12 is a mechanical heart valve and is representative of the set of implantable medical devices such as bioprosthetic and polymer heart valves, suitable for use in the present invention. More particularly, package 10 may also be used with other implantable prosthetic devices such as mechanical heart valves with flexible polymeric or silicone rubber leaflets, such as the heart valve of Purdy et al., U.S. Pat. No. 5,562,729, or vascular grafts, such as the grafts of Lauterjung U.S. Pat. No. 5,824,036 or Lauterjung WO97/48350 (both incorporated herein by reference) or angioplasty rings, such as the rings of Campbell, U.S. Pat. No. 6,102,945 (incorporated herein by reference), or other implantable devices.

Figure 3:
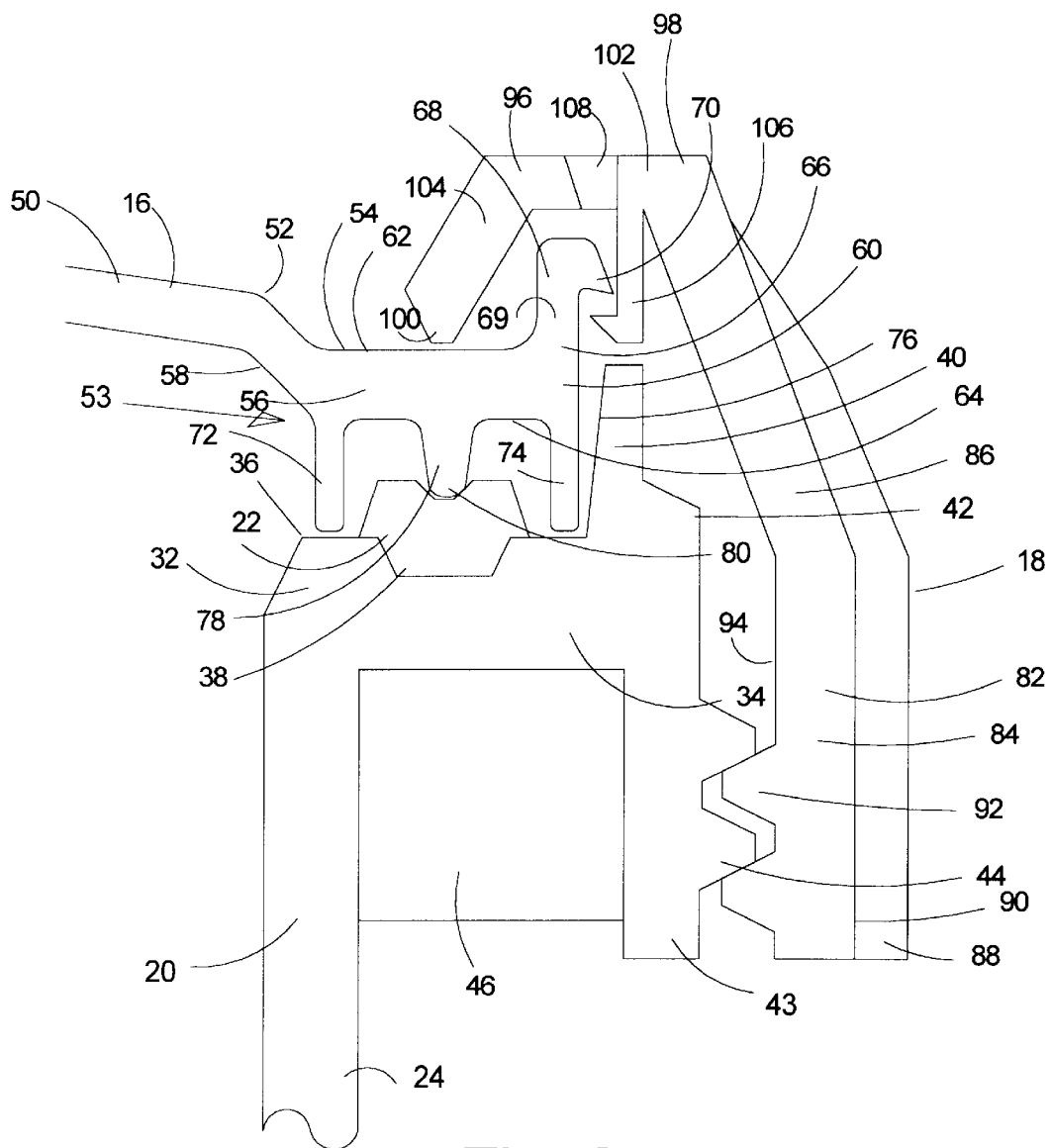
FIG. 3 is a cross sectional view of a region of the container of FIG. 1, taken along line 3—3.

In the illustrated embodiment, the package 10 comprises a jar 14, a lid 16, and an overcap 18. In FIG. 1, a plan through section of these elements is shown in phantom lines. A portion of the plan through section, taken along line 3—3, is also illustrated in FIG. 3.

Figure 2:
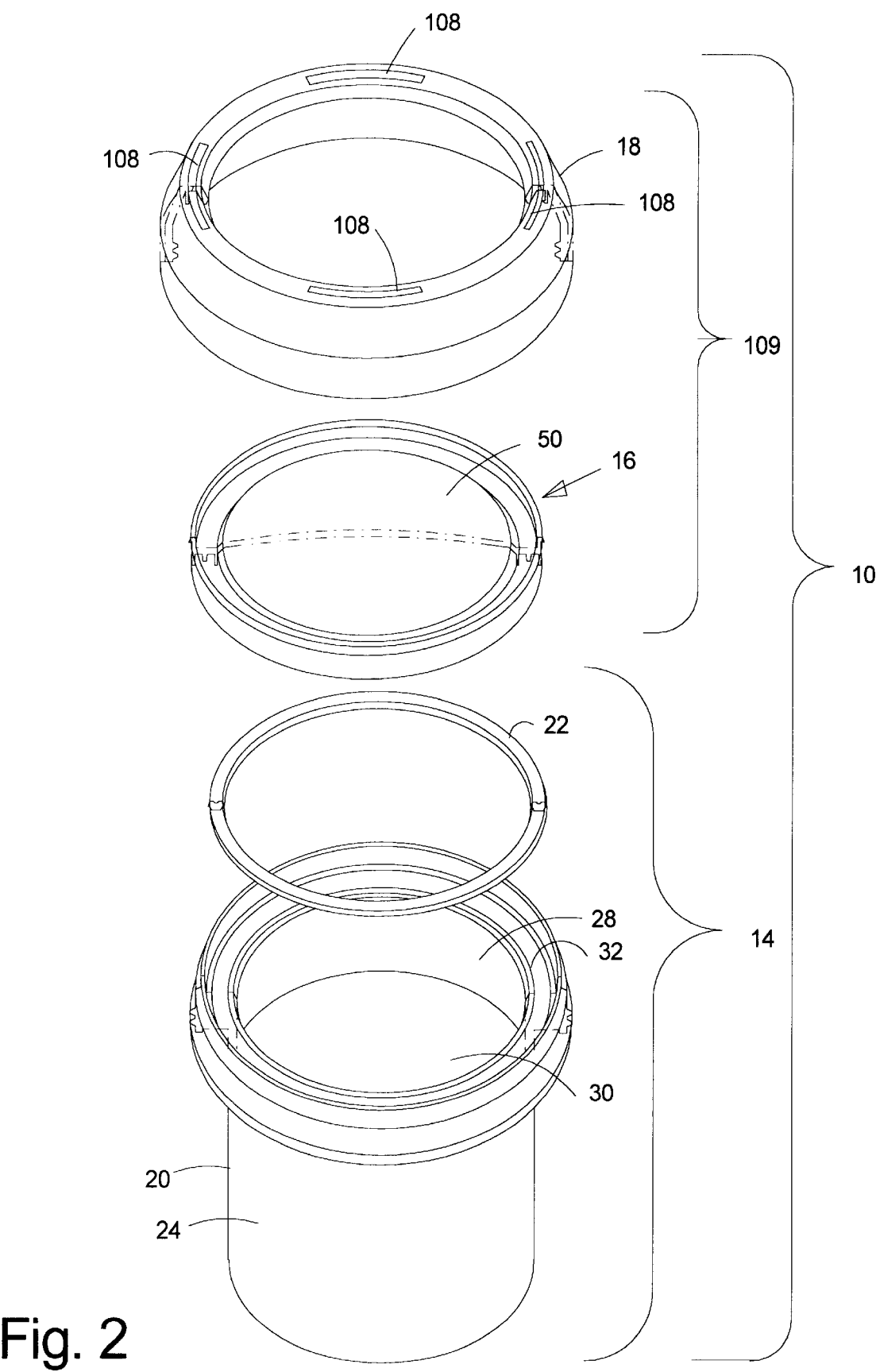
FIG. 2 is an exploded isometric view of the container of FIG. 1.

As shown more fully in FIGS. 1 and 2, the jar 14 comprises two parts, a container 20 and a seal 22. The container has a circumferential wall 24 and a bottom 26 which define an interior 28 that contains the heart valve 12 or other implantable prosthetic device in liquid 30. An upper circumferential edge 32 of the wall 24 abuts the lid 16. A lip 34, generally perpendicular to the wall 24, extends radially outward from the edge 32 and forms an upper surface 36. A circumferential groove 38 in the upper surface 36 receives the seal 22, as will be described more particularly below. A rim 40 at an outer edge 42 of the lip 34 guides the lid 16 into position above the seal 22. A cylindrical flange 43 extends downwardly from the outer edge 42 and supports a set of male threads 44. A plurality of ribs 46 may be provided at periodic intervals between the wall 24 and the cylindrical flange 42. The ribs 46 extend from the wall 24 to the cylindrical flange 43 and provide additional structural support for the cylindrical flange 43 and the lip 34 without significantly increasing the weight of the jar 14.

In a preferred embodiment, the container 20 is cast from a rigid material such as polypropylene, for example Himont 6323 polypropylene homopolymer in a particularly preferred embodiment. The elastometic seal 22 is then placed in the groove 38. Alternatively, the seal 22 can be coupled to the container 20 by casting or another suitable method, and the jar 14 can be manipulated as a single piece, making it easier to assemble the package 10 in a sterile environment such as a glove box. The seal 22 may be comprised of an elastomeric polymer such as Kraton G2705™, available from Advanced Elastomer Systems, Inc., Akron, Ohio. The seal 22 should have a sufficient radial width to accommodate some variation in the placement of the lid 16, as will be explained below. Alternatively, a separate, generally toroidal seal may be placed on the lip 34.

The lid 16 provides a leakproof interior 28 for the jar 14 by engaging the seal 22. The lid 16 comprises a generally circular disc 50 that may be slightly convex. At an outer edge 52 of the disc 50, a seal contact structure 53 extends around the entire periphery of the disc 50. The seal contact structure 53 comprises a ring 56 having an inner edge 58, an outer edge 60, a top surface 62 and a bottom surface 64. At a junction 66 between the top surface 62 and the outer edge 60 there is a circumferential snap hook 68. In the preferred embodiment, the snap hook 68 comprises a cylindrical segment 69 that joins the ring 56 at a lower end of the cylindrical segment to a radially outwardly facing circumferential hook 70. The snap hook 68 extends completely along the outer edge 60 of the lid 16. The snap hook 68 could also be interrupted at selected intervals. Interruptions or breaks in the snap hook 68 would make it easier for the snap hook to be deflected inwardly to engage the overcap 12, as will be described below. Because of the preferred structure of the overcap 12, interruptions of the snap hook 68 are not considered necessary.

In a preferred embodiment, two circumferential, cylindrical legs 72, 74 extend downwardly from the bottom surface 64 of the ring 56. Preferably, an inner leg 72 is near the inner edge 58 of the ring 56 and an outer leg 74 is near the outer edge 60 of the ring 56. In the preferred embodiment, the legs 72, 74 are continuous, but they may be interrupted by gaps or breaks as a matter of design discretion. The two legs 72, 74 are spaced sufficiently far away from each other to allow them to bracket the seal 22 when the lid 16 is placed on the jar 14. The outer leg 74 guides the lid into position over the seal 22 by sliding down an inner surface 76 of the rim 40 on the jar 14. The two legs 72, 74 limit the amount of force applied to seal 22. In an alternative embodiment, the legs 72, 74 are not present and the force applied to seal 22 is controlled by the degree to which the lid 16 is tightened onto jar 14

Between the two legs 72, 74 and extending downwardly from the bottom surface 64 of the ring 56, there is a ridge 78. The ridge 78 is continuous and preferably cylindrical. The ridge 78 is configured to contact the seal 22 when the lid 16 is on the jar 14 along the entire length of the seal, thereby closing the package 10 and providing a barrier sufficient to prevent the loss of liquid from within the package for an extended period of time. A tip 80 of the ridge 78 has a cross sectional radius selected such that the tip will provide sufficient localized contact pressure with the seal when the tip is forced into the seal to produce the desired sealing characteristics. In the embodiment of FIGS. 1–3, legs 72 and 74, as well as ridge 78, are depicted as being integrally formed with the lid 16. Other means of coupling the legs and the ridge to lid 16 are possible without departing from the scope of the invention.

The two legs 72, 74 are sufficiently long to prevent the ridge 78 from being forced too far into the seal 22 and distorting or damaging the seal. Consequently, the lid 16 and jar 14 cooperate to produce a consistent seal with predictable characteristics without elaborate assembly devices. Moreover, when compressed by the overcap 18, as described below, the two legs 72, 74 are preloaded in compression, which compensates for fluctuations in differential pressure across the seal 22 over a range of ambient conditions. Ambient air pressure does not remain constant. After the package 10 is assembled, it may be anticipated that ambient pressure will fall below the pressure in the package 10 from time to time. The preloading of the legs 72, 74 keeps the pressure difference across the lid from moving the tip 80 of the ridge 78 out of the seal 22.

The overcap 18 comprises a circumferential cylindrical wall 82 of any suitable shape. In the preferred embodiment, for example, the wall 82 has a right cylindrical lower section 84 surmounted by a frustro-conical upper section 86. A plurality of vertical ridges 88 may be provided on an outer surface 90 of the wall 82 to improve grip friction when the overcap is turned. Other features to improve grip may be selected by those skilled in the art. A set of female threads 92 on an inner surface 94 of the wall 82 engages the male threads 44 on the jar 14.

A circumferential compression arm 96 extends radially inwardly from an upper edge 98 of the wall 82. The compression arm 96 extends both inwardly from the wall 82 and then down towards the lid 16 so that a tip 100 can exert pressure against the top surface 62 of the seal contact structure 53 substantially directly over the ridge 78 and seal 22.

In the preferred embodiment, the arm 96 comprises a substantially planar flange 102 coupling the wall 82 to a downward facing frustro-conical ring 104. The frustro-conical ring 104 ends at the tip 100 that contacts the lid 16. It is preferred that the arm 96 be circularly continuous to apply uniform pressure completely around the lid 16. Nevertheless, the arm could be interrupted without departing from the teachings of the invention.

The overcap 18 further has one or more snap hooks 106 that extend axially downwardly from the arm 96. The snap hooks 106 could also be attached to the wall 82. The snap hooks 106 on the overcap 18 are configured to engage the snap hook 68 on the lid 16. As noted above, the lid snap hook 68 is preferably circularly continuous. The overcap 18, on the other hand, preferably has a plurality of snap hooks 106 spaced circularly around the overcap. This makes it easier for the overcap snap hooks 106 to bend outwardly as the lid 16 is snapped into the overcap. In addition, a slot 108 may be cut in the arm 96 of the overcap 18 radially inwardly from overcap snap hook 106 to increase the flexibility of the adjacent overcap snap hook 106. In the preferred embodiment, four radially equally spaced slots and snap hooks have been provided on the overcap, as best shown in FIG. 1, but other configurations may be selected. In the embodiments depicted in FIGS. 1–3, the snap hooks 68 and 106 are integrally formed with the lid 16 and the overcap 18, respectively. Other ways of joining the snap hooks to the lid and overcap are possible without departing from the scope of the invention.

In the packaging 10, the lid 16 is snapped into the overcap 18 before sterilization. This provides a cap assembly 109 that is essentially a single piece and is consequently easier to manipulate than two separate pieces would be. Moreover, the anti-microbial packaging 10 should provide a consistent, reliable seal, but should also be relatively easy to open. The unitary overcap-and-lid configuration described herein reduces the initial torque needed to start opening the packaging 10 because one must only overcome the contact friction between the tip 100 of the arm 96 of the overcap and the top surface 62 of the seal contact structure 52 of the lid, rather than the contact friction between the seal 22 and the tip 80 of the ridge 78. The seal 22 is elastomeric and the ridge 78 and seal are in continuous contact, whereas both the top surface 62 and the arm tip 100 may be relatively hard and have a low coefficient of friction and a relatively small contact area. This makes the task of opening the packaging easier, even after a long self-life.

Figure 4:
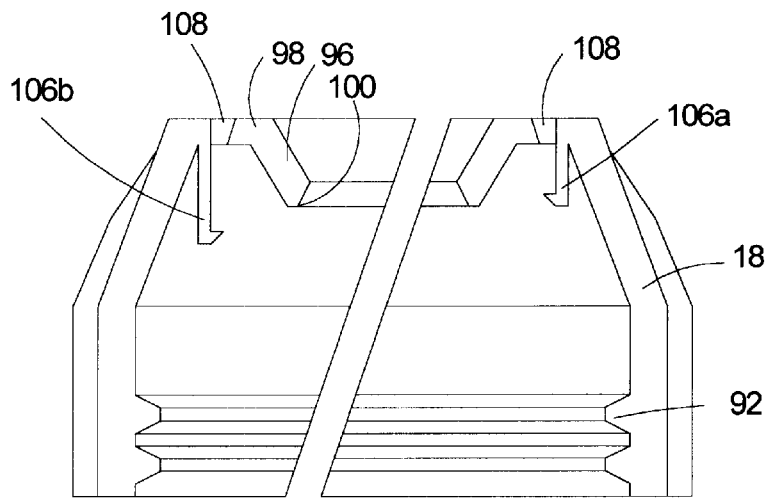
FIG. 4 is a partial cross-sectional view of an overcap for the container of FIG. 1.

Moreover, the snap locks 106 may have different lengths, as illustrated in FIG. 4. When the overcap is unscrewed, the shortest snap lock 106a would begin to raise the lid first. If the lid is being held on the jar by an ambient atmospheric overpressure, the short snap lock 106a would begin to raise only a part of the lid, thus allowing the force developed by unscrewing the lid to be applied at a small part of the edge of the lid until the contact between the ridge 78 and the seal 22 has been broken and the pressure on both sides of the lid equalize. Thereafter, longer snap hooks 106b would raise the remaining portion of the lid.

Figure 5:
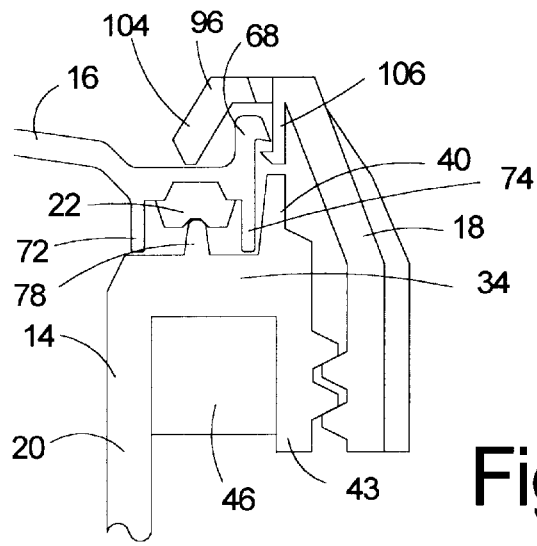
FIG. 5 is a cross-sectional view of an alternative embodiment for the region of FIG. 3 for the container of FIG. 1.
Figure 6:
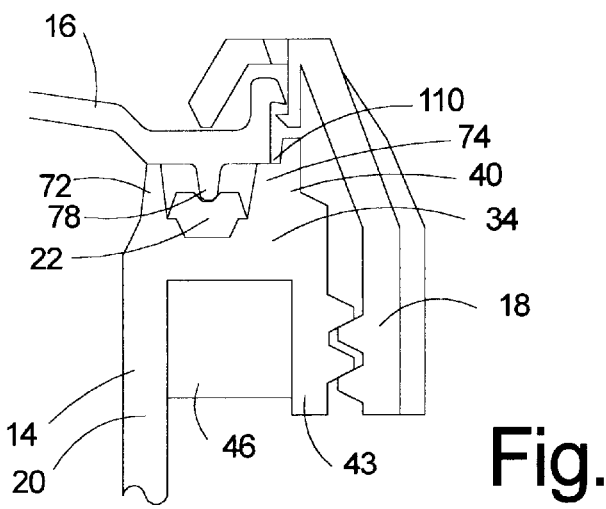
FIG. 6 is a cross-sectional view of a second alternative embodiment for the region of FIG. 3 for the container of FIG. 1.

The embodiment of FIGS. 1 through 4 represent the preferred embodiment of the invention, but variations will suggest themselves to those of skill in the art. For example, as suggested by FIG. 5, the seal 22 could be incorporated into the lid 16 rather than the jar 14, and the ridge 78 could be incorporated into the jar 14. FIG. 6 suggests another variation, wherein the legs 72, 74 are incorporated into the jar 14 rather than the lid 16. Moreover, the outside leg 74 may be combined with the rim 40 and a ledge 110 may function as the outside leg 74 of the ring 56. Other variations will suggest themselves to those of skill in the art in view of the teachings presented herein.

The foregoing descriptions concern preferred embodiments of the invention and are given by way of example only. The invention is not limited to any of the specific features described herein, but includes all variations thereof within the scope of the appended claims.

What is claimed is:

1. A package for an implantable prosthetic device, the package comprising a jar having an upper edge circumscribing an opening into said jar, and a lid assembly adapted to be removably coupled to said jar, said lid assembly comprising:
   (a) an overcap comprising a bottom surface;
   (b) a lid, coupled to said overcap, comprising an upper surface;
   (c) a connector for coupling said lid to said overcap, said connector comprising
      (1) at least a first snap hook extending downwardly from said overcap, and
      (2) at least a second snap hook, adapted to engage said first snap hook, extending upwardly from said lid, wherein at least one of said first snap hook and said second snap hook comprises a plurality of snap hooks, and wherein at least one snap hook of said plurality of snap hooks is of a different length than the remainder of said plurality of snap hooks; and
   (d) a seal interposed between said lid and said upper edge of said jar.

2. The package of claim 1, wherein said lid further comprises a ridge configured to press into said seal when said lid assembly is coupled to said jar.

3. The package of claim 2 further comprising an inner leg spaced radially inwardly from said ridge and said seal and an outer leg spaced radially outwardly from said ridge and said seal.

4. The package of claim 2 wherein said overcap further comprises an arm configured to press said ridge into said seal.

5. The package of claim 4 further comprising an inner leg spaced radially inwardly from said ridge and said seal and an outer leg spaced radially outwardly from said ridge and said seal.

6. The package of claim 5 wherein said legs are circumferentially continuous.

7. The package of claim 6 wherein said legs are integrally formed with said lid.

8. The package of claim 7 further comprising a groove in said upper edge of said jar, said seal being received in said groove.

9. The package of claim 8 further comprising a rim on said upper edge of said jar, said rim being spaced radially outwardly from said groove and seal and said outer leg being received between said seal and said rim.

10. The package of claim 9 wherein said overcap further comprises at least one slot adjacent to a snap hook on said overcap.

11. A package for an implantable prosthetic device comprising a jar having an upper edge circumscribing an opening into said jar, and a lid assembly adapted to be removably coupled to said jar, wherein said lid assembly comprises:
   (a) a lid;
   (b) a seal interposed between said lid and said upper edge of said jar;
   (c) a ridge configured to press into said seal when said lid assembly is coupled to said jar; and
   (d) an overcap adapted to be coupled to said jar wherein said overcap comprises an arm configured to press said ridge into said seal,
   wherein the package comprises (i) an inner leg spaced radially inwardly from said ridge and said seal and (ii) an outer leg spaced radially outwardly from said ridge and said seal, said legs being circumferentially continuous and integrally formed with said lid; and
   wherein the package further comprises a groove in said upper edge of said jar, said seal being received in said groove.

12. The package of claim 11 further comprising a rim on said upper edge of said jar, said rim being spaced radially outwardly from said groove and seal and said outer leg being received between said seal and said rim.

13. A package for an implantable prosthetic device, the package comprising a jar having an upper edge circumscribing an opening into said jar, and a lid assembly removably received on said jar, wherein said lid assembly comprises:
   (a) an overcap having a bottom surface and a generally annular configuration defining an interior area, said overcap being adapted to be coupled to said jar and comprising an arm extending into said interior area;
   (b) a lid pressed against said upper edge of said jar by said arm of said overcap and wherein said lid comprises an upper surface;
   (c) a groove in said upper edge of said jar;
   (d) a seal interposed between said lid and said upper surface of said jar received in said groove; and
   (e) a ridge configured to press into said seal when said lid assembly is received on said jar.

14. The package of claim 13 further comprising a connector rotatably connecting said lid to said overcap, said connector comprising a first snap hook extending downwardly from said overcap, and a second snap hook adapted to engage said first snap hook and extending upwardly from said lid.

15. The package of claim 14 wherein at least one of said first and said second snap hooks comprises a plurality of snap hooks.

16. The package of claim 15 wherein said plurality of snap hooks is integrally formed with said overcap.

17. The package of claim 16 wherein at least one of said plurality of snap hooks is shorter than at least some of said plurality of snap hooks.

18. The package of claim 17 further comprising a ridge configured to press into said seal when said lid assembly is received on said jar.

19. The package of claim 18 further comprising a groove in said upper edge of said jar, said seal being received in said groove.

20. The package of claim 19 further comprising a rim on said upper edge of said jar, said rim being spaced radially outwardly from said groove and seal.

21. A package for an implantable prosthetic device comprising:
   (a) a jar comprising a circumferential wall and an upper edge defining an opening of the jar;

(b) a lid assembly comprising:
  (1) an over cap comprising an upper and lower surface; and
  (2) a lid comprising an upper and lower surface coupled to the overcap,
wherein said lid assembly is capable of being coupled to the jar to close the jar by coupling the overcap to the circumferential wall of the jar; and
(c) a seal having an upper and lower surface capable of sealing the jar by cooperation between
  (1) the lower surface of the lid and the upper surface of seal: and
  (2) the lower surface of the seal and the upper edge of the jar, when the overcap is coupled to the circumferential wall of the jar,
wherein the overcap is coupled to the lid by the cooperation of at least one snap hook extending from the overcap and at least one snap hook extending from the upper surface of the lid.

22. The package of claim 21 wherein the upper and lower surfaces of the seal are substantially parallel to the upper and lower surfaces of the overcap when the overcap is coupled to the circumferential wall of the jar.

23. The package of claim 21 wherein a ridge formed on the lower surface of said lid is configured to deform the seal to facilitate sealing of the jar when the overcap is coupled to the circumferential wall of the jar.

24. The package of claim 23 wherein the overcap is capable of being coupled to the circumferential wall of the container by the interaction of threads formed in the overcap and threads formed in the jar.

25. The package of claim 21 wherein the overcap comprises a plurality of snap hooks.

26. The package of claim 25 wherein the plurality of snap hooks are integrally formed in the overcap.

27. The package of claim 26 wherein the at least one of the plurality of snap hooks is of a different length than the remainder of the plurality of snap hooks.

28. A package for an implantable prosthetic device comprising:
(a) an implantable prosthetic device container comprising a lip, a circumferential wall and an upper edge defining an opening of the container;
(b) a lid assembly comprising:
  (1) an overcap comprising an upper and lower surface, and
  (2) a lid comprising an upper and lower surface coupled to the overcap,
wherein said lid assembly is coupled to the container by cooperation of the overcap with the lip of the container; and
(c) a seal having an upper surface cooperating with the lower surface of the lid and a lower surface cooperating with the upper edge of the container, wherein the overcap is coupled to the lid by the cooperation of at least one snap hook extending from the lower surface of the overcap and at least one snap hook extending from the upper surface of the lid.

29. The package of claim 28 wherein the upper and lower surfaces of the seal are substantially parallel to the upper and lower surfaces of the overcap.

30. The package of claim 29 wherein the overcap is coupled to the circumferential wall of the container by the interaction of a thread formed in the overcap and a thread formed in the container.

31. The package of claim 28 wherein the overcap comprises a plurality of snap hooks.

32. The package of claim 31 wherein the plurality of snap hooks are integrally formed in the overcap.

33. The package of claim 32 wherein the at least one of the plurality of snap hooks is of a different length than the remainder of the plurality of snap hooks.

* * * * *